United States Patent
Plakogiannis et al.

(10) Patent No.: US 12,409,132 B2
(45) Date of Patent: *Sep. 9, 2025

(54) TRANSDERMAL DELIVERY OF DRONABINOL

(71) Applicant: Pike Therapeutics USA, Inc., Wilmington, DE (US)

(72) Inventors: Fotios M. Plakogiannis, Whitestone, NY (US); Tamanna Lather, Jersey City, NJ (US); Nisarg Modi, Jersey City, NJ (US); Marina Borovinskaya, East Brunswick, NJ (US)

(73) Assignee: Pike Therapeutics USA, Inc., Wilmington, DE (US)

( * ) Notice: Subject to any disclaimer, the term of this patent is extended or adjusted under 35 U.S.C. 154(b) by 938 days.

This patent is subject to a terminal disclaimer.

(21) Appl. No.: 17/221,667

(22) Filed: Apr. 2, 2021

(65) Prior Publication Data
US 2021/0220325 A1    Jul. 22, 2021

(51) Int. Cl.
| | |
|---|---|
| *A61K 31/352* | (2006.01) |
| *A61K 9/00* | (2006.01) |
| *A61K 9/70* | (2006.01) |
| *A61P 1/08* | (2006.01) |
| *A61P 3/04* | (2006.01) |

(52) U.S. Cl.
CPC .......... *A61K 9/0021* (2013.01); *A61K 9/0014* (2013.01); *A61K 9/703* (2013.01); *A61K 9/7084* (2013.01); *A61K 31/352* (2013.01); *A61P 1/08* (2018.01); *A61P 3/04* (2018.01)

(58) Field of Classification Search
CPC .... A61K 9/0021; A61K 9/0014; A61K 9/703; A61K 9/7084; A61K 31/352; A61P 3/04; A61P 1/08
USPC ...................................................... 514/455
See application file for complete search history.

(56) References Cited

U.S. PATENT DOCUMENTS

| | | | |
|---|---|---|---|
| 5,804,592 A | 9/1998 | Volicer | |
| 6,113,940 A | 9/2000 | Brooke et al. | |
| 6,245,347 B1 | 6/2001 | Zhang et al. | |
| 6,328,992 B1 | 12/2001 | Brooke et al. | |
| 6,689,379 B1 | 2/2004 | Bracht | |
| 6,946,150 B2 | 9/2005 | Whittle | |
| 7,025,992 B2 | 4/2006 | Whittle et al. | |
| 7,544,676 B2 | 6/2009 | Dolle et al. | |
| 7,592,328 B2 | 9/2009 | Jarho et al. | |
| 7,622,140 B2 | 11/2009 | Whittle et al. | |
| 7,671,052 B2 | 3/2010 | Dolle et al. | |
| 7,709,536 B2 | 5/2010 | Whittle | |
| 7,807,711 B2 | 10/2010 | Korthout et al. | |
| 7,968,594 B2 | 6/2011 | Guy et al. | |
| 8,071,641 B2 | 12/2011 | Weiss et al. | |
| 8,211,946 B2 | 7/2012 | Whittle | |
| 8,246,981 B2 | 8/2012 | Patel et al. | |
| 8,293,786 B2 | 10/2012 | Stinchcomb et al. | |
| 8,435,556 B2 | 5/2013 | Stinchcomb et al. | |
| 8,449,908 B2 | 5/2013 | Stinchcomb et al. | |
| 8,481,085 B2 | 7/2013 | Musty et al. | |
| 8,603,515 B2 | 12/2013 | Whittle | |
| 8,642,645 B2 | 2/2014 | Kelly | |
| 8,771,760 B2 | 7/2014 | Guy et al. | |
| 8,992,908 B2 | 3/2015 | Smith et al. | |
| 9,029,423 B2 | 5/2015 | Whittle | |
| 9,034,395 B2 | 5/2015 | Whittle et al. | |
| 9,205,063 B2 | 12/2015 | Guy et al. | |
| 9,304,134 B2 | 4/2016 | Smith | |
| 9,375,417 B2 | 6/2016 | Smith et al. | |
| 9,533,942 B2 | 1/2017 | Stinchcomb et al. | |
| 9,603,887 B2 | 3/2017 | Kelly | |
| 9,763,912 B2 | 9/2017 | Chen et al. | |
| 9,833,433 B1 | 12/2017 | Chen et al. | |
| 9,918,961 B2 | 3/2018 | Hearn et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 9,957,321 B2 | 5/2018 | Smith et al. | |
| 9,962,340 B2 | 5/2018 | Weimann | |
| 9,962,341 B2 | 5/2018 | Stott et al. | |
| 10,004,684 B2 | 6/2018 | Whittle et al. | |
| 10,028,904 B2 | 7/2018 | Smith et al. | |
| 10,092,525 B2 | 10/2018 | Guy et al. | |

(Continued)

FOREIGN PATENT DOCUMENTS

| | | |
|---|---|---|
| CA | 2859930 A1 | 3/2016 |
| CA | 2978605 A1 | 9/2016 |

(Continued)

OTHER PUBLICATIONS

Alper, Kenneth et al., "The ibogaine medical subculture", Journal Of Ethsopharmacology, vol. 115(1), p. 9-24, 2008.

(Continued)

*Primary Examiner* — Kristin A Vajda
(74) *Attorney, Agent, or Firm* — Potomac Law Group, PLLC; Joseph F. Murphy

(57) ABSTRACT

Provided is a transdermal drug delivery system comprising dronabinol. The dronabinol transdermal delivery system provides a drug plasma concentration at predetermined rate for a predetermined period of time, offering a simplified therapeutic regimen by decreasing dosing frequency for the treatment and/or prevention of nausea and/or vomiting associated with, for example, chemotherapy.

4 Claims, 1 Drawing Sheet

(56) References Cited

U.S. PATENT DOCUMENTS

| | | |
|---|---|---|
| 10,098,867 B2 | 10/2018 | Javid et al. |
| 10,098,895 B2 | 10/2018 | Chang et al. |
| 10,111,840 B2 | 10/2018 | Guy et al. |
| 10,118,006 B2 | 11/2018 | Davidson et al. |
| 10,137,095 B2 | 11/2018 | Guy et al. |
| 10,155,018 B1 | 12/2018 | Jenn |
| 10,172,809 B2 | 1/2019 | Aung-Din |
| 10,195,159 B2 | 2/2019 | Whittle et al. |
| 10,213,390 B1 | 2/2019 | Bonn-Miller et al. |
| 10,272,125 B2 | 4/2019 | Weimann |
| 10,278,996 B2 | 5/2019 | Avidov et al. |
| 10,307,392 B2 | 6/2019 | Kariman |
| 10,314,792 B2 | 6/2019 | Sebree et al. |
| 10,383,816 B2 | 8/2019 | Aung-Din |
| 10,413,521 B2 | 9/2019 | Hearn et al. |
| 10,420,809 B2 | 9/2019 | Crowley |
| 10,471,022 B2 | 11/2019 | Bonn-Miller et al. |
| 10,538,373 B2 | 1/2020 | Whittle |
| 10,555,927 B2 | 2/2020 | Jenn |
| 10,568,848 B2 | 2/2020 | Sebree et al. |
| RE47,885 E | 3/2020 | Strinchcomb et al. |
| 10,588,869 B2 | 3/2020 | Weimann |
| 10,588,871 B1 | 3/2020 | Fracassi et al. |
| 10,588,974 B2 | 3/2020 | Leone-Bay et al. |
| 10,603,288 B2 | 3/2020 | Guy et al. |
| 10,617,733 B2 | 4/2020 | Kelly |
| 10,632,064 B2 | 4/2020 | Aung-Din |
| 10,660,872 B2 | 5/2020 | Sarne |
| 10,675,240 B2 | 6/2020 | Smith et al. |
| 10,675,264 B2 | 6/2020 | Green et al. |
| 10,695,287 B2 | 6/2020 | Robbins et al. |
| 10,709,671 B2 | 7/2020 | Guy et al. |
| 10,709,673 B2 | 7/2020 | Guy |
| 10,709,674 B2 | 7/2020 | Guy et al. |
| 10,709,748 B2 | 7/2020 | Witowski et al. |
| 10,716,766 B2 | 7/2020 | Aung-Din |
| 10,751,299 B2 | 8/2020 | Ghalili |
| 10,758,497 B2 | 9/2020 | Bonn-Miller et al. |
| 10,758,514 B2 | 9/2020 | Liu et al. |
| 10,799,545 B2 | 10/2020 | Weimann |
| 10,807,777 B2 | 10/2020 | Whittle |
| 10,828,266 B2 | 11/2020 | Aung-Din |
| 10,849,860 B2 | 12/2020 | Guy et al. |
| 10,864,189 B2 | 12/2020 | Borok |
| 10,869,842 B1 | 12/2020 | Summers |
| 10,881,606 B2 | 1/2021 | Schmitz et al. |
| 10,918,608 B2 | 2/2021 | Guy et al. |
| 10,918,686 B2 | 2/2021 | Siurkus |
| 10,945,967 B2 | 3/2021 | Song |
| 10,966,939 B2 | 4/2021 | Guy et al. |
| 11,026,896 B2 | 6/2021 | Fitzsimmons et al. |
| 11,052,055 B2 | 7/2021 | Kochinke |
| 11,065,209 B2 | 7/2021 | Guy et al. |
| 11,065,227 B2 | 7/2021 | Stott et al. |
| 11,096,905 B2 | 8/2021 | Guy et al. |
| 11,116,730 B2 | 9/2021 | Fracassi et al. |
| 11,147,799 B2 | 10/2021 | Kopsky et al. |
| 11,154,516 B2 | 10/2021 | Guy et al. |
| 11,154,517 B2 | 10/2021 | Guy et al. |
| 11,160,795 B2 | 11/2021 | Guy et al. |
| 11,207,292 B2 | 12/2021 | Guy et al. |
| 2002/0019421 A1 | 2/2002 | Biberman |
| 2002/0111377 A1 | 8/2002 | Stinchcomb |
| 2004/0033254 A1 | 2/2004 | Song et al. |
| 2004/0138293 A1 | 7/2004 | Werner et al. |
| 2005/0042271 A1 | 2/2005 | Xiong et al. |
| 2005/0070596 A1 | 3/2005 | Baker et al. |
| 2006/0039959 A1 | 2/2006 | Wessling |
| 2006/0135599 A1 | 6/2006 | Symonds et al. |
| 2007/0060638 A1 | 3/2007 | Olmstead et al. |
| 2007/0072939 A1 | 3/2007 | Kupper |
| 2007/0083186 A1 | 4/2007 | Carter et al. |
| 2008/0112895 A1 | 5/2008 | Kottayil et al. |
| 2009/0197941 A1 | 8/2009 | Guy et al. |
| 2009/0298929 A1 | 12/2009 | Jarho et al. |
| 2010/0035978 A1 | 2/2010 | Guy et al. |
| 2010/0168108 A1 | 7/2010 | Dolle et al. |
| 2010/0184848 A1 | 7/2010 | Wine et al. |
| 2010/0273895 A1 | 10/2010 | Stinchcomb et al. |
| 2010/0286098 A1 | 11/2010 | Robson et al. |
| 2010/0317729 A1 | 12/2010 | Guy et al. |
| 2011/0021617 A1 | 1/2011 | Korthout et al. |
| 2011/0052694 A1 | 3/2011 | Stinchcomb et al. |
| 2011/0097393 A1 | 4/2011 | Al-Ghananeem |
| 2012/0034293 A1 | 2/2012 | Stinchcomb et al. |
| 2013/0022687 A1 | 1/2013 | Fitzgerald, Jr. et al. |
| 2013/0122077 A1 | 5/2013 | Al-Ghananeem |
| 2013/0210786 A1 | 8/2013 | Howson |
| 2013/0245110 A1 | 9/2013 | Guy et al. |
| 2013/0253449 A1 | 9/2013 | Yoshitake et al. |
| 2014/0039043 A1 | 2/2014 | Musty et al. |
| 2014/0314757 A1 | 10/2014 | Sanchez et al. |
| 2015/0265720 A1 | 9/2015 | Levine et al. |
| 2015/0297556 A1 | 10/2015 | Smith |
| 2015/0342902 A1 | 12/2015 | Vangara et al. |
| 2015/0343071 A1 | 12/2015 | Vangara et al. |
| 2016/0000843 A1 | 1/2016 | Lowe et al. |
| 2016/0022627 A2 | 1/2016 | Smith |
| 2016/0039591 A1 | 2/2016 | Kinzer |
| 2016/0220593 A1 | 8/2016 | Anastassov et al. |
| 2016/0228385 A1 | 8/2016 | Sievers et al. |
| 2016/0256411 A1 | 9/2016 | Aung-Din |
| 2016/0271252 A1 | 9/2016 | Vangara et al. |
| 2016/0338974 A1 | 11/2016 | Aung-Din |
| 2016/0361271 A1 | 12/2016 | Weimann |
| 2017/0042791 A1 | 2/2017 | Ghalili et al. |
| 2017/0071870 A1 | 3/2017 | Weimann |
| 2017/0202895 A1 | 7/2017 | Hugh |
| 2017/0273914 A1 | 9/2017 | Knudsen |
| 2017/0306013 A1 | 10/2017 | Clark et al. |
| 2018/0004994 A1 | 1/2018 | Bottazzi et al. |
| 2018/0021247 A1 | 1/2018 | Ghalili et al. |
| 2018/0042842 A1 | 2/2018 | Whittle et al. |
| 2018/0042845 A1 | 2/2018 | Sinai et al. |
| 2018/0071210 A1 | 3/2018 | Wilkhu et al. |
| 2018/0078512 A1 | 3/2018 | Weimann |
| 2018/0169035 A1 | 6/2018 | Eyal |
| 2018/0284402 A1 | 10/2018 | Hoag |
| 2018/0289665 A1 | 10/2018 | Turner et al. |
| 2018/0311180 A1 | 11/2018 | Kochinke |
| 2018/0311181 A1 | 11/2018 | Kochinke |
| 2018/0311184 A1 | 11/2018 | Hoag |
| 2018/0318529 A1 | 11/2018 | Davidson et al. |
| 2018/0353463 A1 | 12/2018 | Winnicki |
| 2018/0360757 A1 | 12/2018 | Doroudian et al. |
| 2018/0369191 A1 | 12/2018 | Muscarella |
| 2019/0023780 A1 | 1/2019 | Smith et al. |
| 2019/0083388 A1 | 3/2019 | Gutterman et al. |
| 2019/0105298 A1 | 4/2019 | Eyal |
| 2019/0110981 A1 | 4/2019 | Weimann |
| 2019/0117617 A1 | 4/2019 | Kariman |
| 2019/0125779 A1 | 5/2019 | Ziburkus et al. |
| 2019/0133994 A1 | 5/2019 | Smith et al. |
| 2019/0134121 A1 | 5/2019 | Bermudez et al. |
| 2019/0167583 A1 | 6/2019 | Shah |
| 2019/0201372 A1 | 7/2019 | McKay |
| 2019/0224118 A1 | 7/2019 | Navon et al. |
| 2019/0224140 A1 | 7/2019 | Guy et al. |
| 2019/0231826 A1 | 8/2019 | Avidov et al. |
| 2019/0255014 A1 | 8/2019 | Gardner |
| 2019/0298683 A1 | 10/2019 | Friedman |
| 2019/0314297 A1 | 10/2019 | Gallily |
| 2019/0321355 A1 | 10/2019 | Anavi-Goffer |
| 2019/0321426 A1 | 10/2019 | Gallily |
| 2019/0328884 A1 | 10/2019 | Jones, Jr. et al. |
| 2019/0365667 A1 | 12/2019 | Wright et al. |
| 2020/0038421 A1 | 2/2020 | Anastassov et al. |
| 2020/0054887 A1 | 2/2020 | Levin |
| 2020/0078332 A1 | 3/2020 | Leone-Bay et al. |
| 2020/0085816 A1 | 3/2020 | Raz |
| 2020/0093755 A1 | 3/2020 | Biro et al. |
| 2020/0108027 A1 | 4/2020 | Whalley et al. |
| 2020/0129741 A1 | 4/2020 | Kawwas et al. |
| 2020/0138771 A1 | 5/2020 | Diez et al. |

(56) References Cited

U.S. PATENT DOCUMENTS

| | | |
|---|---|---|
| 2020/0138773 A1 | 5/2020 | Jenn |
| 2020/0163980 A1 | 5/2020 | Dellinger |
| 2020/0170963 A1 | 6/2020 | Tich et al. |
| 2020/0188324 A1 | 6/2020 | Sebree et al. |
| 2020/0188348 A1 | 6/2020 | Sinai et al. |
| 2020/0206184 A1 | 7/2020 | Robson et al. |
| 2020/0214995 A1 | 7/2020 | Sebree et al. |
| 2020/0215136 A1 | 7/2020 | Naheed |
| 2020/0237683 A1 | 7/2020 | Whalley et al. |
| 2020/0253919 A1 | 8/2020 | Raz et al. |
| 2020/0261376 A1 | 8/2020 | Yu et al. |
| 2020/0261404 A1 | 8/2020 | Raz et al. |
| 2020/0276132 A1 | 9/2020 | Weimann |
| 2020/0297656 A1 | 9/2020 | Guy et al. |
| 2020/0330379 A1 | 10/2020 | Singh et al. |
| 2020/0338041 A1 | 10/2020 | Smith et al. |
| 2020/0338151 A1 | 10/2020 | Witowski et al. |
| 2020/0345653 A1 | 11/2020 | Hansen et al. |
| 2020/0345655 A1 | 11/2020 | Heinzerling et al. |
| 2020/0345657 A1 | 11/2020 | Lurya et al. |
| 2020/0345685 A1 | 11/2020 | Otiko |
| 2020/0352849 A1 | 11/2020 | Rotunda |
| 2020/0352901 A1 | 11/2020 | Raber et al. |
| 2020/0360299 A1 | 11/2020 | Bonn-Miller et al. |
| 2020/0384048 A1 | 12/2020 | Kariman |
| 2020/0384049 A1 | 12/2020 | Kariman |
| 2021/0015740 A1 | 1/2021 | Greenspan et al. |
| 2021/0023044 A1 | 1/2021 | Spirtos |
| 2021/0030777 A1 | 2/2021 | Maida |
| 2021/0052512 A1 | 2/2021 | Guy et al. |
| 2021/0052545 A1 | 2/2021 | Jones, Jr. et al. |
| 2021/0059976 A1 | 3/2021 | Wilkhu et al. |
| 2021/0069333 A1 | 3/2021 | Diez et al. |
| 2021/0077421 A1 | 3/2021 | Sebree et al. |
| 2021/0100737 A1* | 4/2021 | Plakogiannis ............ A61P 1/08 |
| 2021/0106540 A1 | 4/2021 | Plakogiannis et al. |
| 2021/0137833 A1 | 5/2021 | Wang et al. |
| 2021/0145764 A1 | 5/2021 | Lephart |
| 2021/0177937 A1 | 6/2021 | Triebel et al. |
| 2021/0186860 A1 | 6/2021 | Weimann |
| 2021/0196669 A1 | 7/2021 | Schleider et al. |
| 2021/0220325 A1 | 7/2021 | Plakogiannis et al. |
| 2021/0236417 A1* | 8/2021 | Plakogiannis ....... A61K 9/7084 |
| 2021/0244680 A1 | 8/2021 | Kassab et al. |
| 2021/0244683 A1 | 8/2021 | Chaiyasate |
| 2021/0244684 A1 | 8/2021 | Ghalili et al. |
| 2021/0290565 A1 | 9/2021 | Guy et al. |
| 2021/0308070 A1 | 10/2021 | Summers |
| 2021/0308072 A1 | 10/2021 | Wright et al. |
| 2021/0379011 A1 | 12/2021 | Guynn |
| 2021/0386684 A1 | 12/2021 | Weimann |
| 2021/0386685 A1 | 12/2021 | Weimann |
| 2021/0401766 A1 | 12/2021 | Rhodes et al. |
| 2021/0401770 A1 | 12/2021 | Fracassi et al. |
| 2021/0401771 A1 | 12/2021 | Guy et al. |
| 2022/0062211 A1 | 3/2022 | Stott et al. |

FOREIGN PATENT DOCUMENTS

| | | |
|---|---|---|
| EP | 2609912 A1 | 7/2013 |
| JP | 2011505382 A | 2/2011 |
| WO | 2001003668 A1 | 1/2001 |
| WO | 2001064149 A1 | 9/2001 |
| WO | 2002064109 A2 | 8/2002 |
| WO | 2002069993 A1 | 9/2002 |
| WO | 2002089945 A2 | 11/2002 |
| WO | 2003105800 A2 | 12/2003 |
| WO | 2004016246 A1 | 2/2004 |
| WO | 2006041841 A1 | 4/2006 |
| WO | 2006044645 A2 | 4/2006 |
| WO | 2006124698 A2 | 11/2006 |
| WO | 2006044645 A3 | 12/2006 |
| WO | 2007001891 A1 | 1/2007 |
| WO | 2008024408 A2 | 2/2008 |
| WO | 2008024490 A2 | 2/2008 |
| WO | 2008039179 A1 | 4/2008 |
| WO | 2008063625 A2 | 5/2008 |
| WO | 2008129258 A1 | 10/2008 |
| WO | 2009020666 A1 | 2/2009 |
| WO | 2009073633 A1 | 6/2009 |
| WO | 2010126501 A1 | 11/2010 |
| WO | 2011026144 A1 | 3/2011 |
| WO | 2013108254 A1 | 7/2013 |
| WO | 2015025312 A1 | 2/2015 |
| WO | 2015161165 A1 | 10/2015 |
| WO | 2016090287 A2 | 6/2016 |
| WO | 2016141056 A1 | 9/2016 |
| WO | 2018048789 A1 | 3/2018 |
| WO | 2018071452 A1 | 4/2018 |
| WO | 2018071581 A1 | 4/2018 |
| WO | 2018135943 A1 | 7/2018 |
| WO | 2019058261 A1 | 3/2019 |
| WO | 2019130215 A1 | 7/2019 |
| WO | 2019210287 A1 | 10/2019 |
| WO | 2020016581 A1 | 1/2020 |
| WO | 2020016582 A1 | 1/2020 |
| WO | 2020123625 A1 | 6/2020 |
| WO | 2020128767 A1 | 6/2020 |
| WO | 2020136593 A1 | 7/2020 |
| WO | 2020142692 A1 | 7/2020 |
| WO | 2020152438 A1 | 7/2020 |
| WO | 2020157569 A1 | 8/2020 |
| WO | 2020183350 A1 | 9/2020 |
| WO | 2020198252 A1 | 10/2020 |
| WO | 2020198883 A1 | 10/2020 |
| WO | 2020257538 A1 | 12/2020 |
| WO | 2021003467 A1 | 1/2021 |
| WO | 2021023351 A1 | 2/2021 |
| WO | 2021055499 A1 | 3/2021 |
| WO | 2021070120 A1 | 4/2021 |
| WO | 2021177940 A1 | 9/2021 |
| WO | 2021236782 A1 | 11/2021 |
| WO | 2022118290 A1 | 6/2022 |

OTHER PUBLICATIONS

ASI., "Adhesives Transdermal Delivery Systems", 2005, retrieved from AdhesivesMag.com, Nov. 1, 2005, retrieved from Web Archive Oct. 5, 2016, https://web.archive.org/web/20161005045648/https://www.adhesivemag.com/articles/86012-adhesives-in-transdermal-drug-delivery-systems.

Beug, Michael et al., "Psilocybin and Psilocin Levels in Twenty Species From Seven Genera of Wild Mushrooms in the Pacific Northwest, U.S.A.", Journal of Ethnopharmacology vol. 5(3), p. 271-285, 1982.

Cameron, Lindsay et al., "Psychedelic Microdosing: Prevalence and Subjective Effects", Journal of Psychoactive Drugs vol. 52(2), p. 113-122, 2020.

Center for Drug Evaluation and Research, Application No. 210365Orig1s000; Non Clinical Reviews; Submission date: Jun. 23, 2017.

Glick, Stanley et al., "18-Methoxycoronaridine (18-MC) and ibogaine: Comparsion of Antiaddictive Effiacy Toxicity, and Mechanisms of Action", Annals of the New York Academy of Sciences, vol. 914(1) p. 369-386, 2006.

International Preliminary Report on Patentability for PCT/IB2021/057474 dated Mar. 2, 2023.

International Preliminary Report on Patentability for PCT/IB2021/057483 dated Mar. 2, 2023.

International Search Report and Written Opinion for International Application No. PCT/US2022/053271 mailed Jul. 12, 2022.

International Search Report for PCT/IB2022/053271 mailed Jul. 12, 2022.

International Search Report mailed on Dec. 9, 2021 for PCT/IB2021/057474.

Jensen, Bjorn et al., "Medical Marijuana and Chronic Pain: a Review of Basic Science and Clinical Evidence", Curr Pain Headache Rep. 2015.

Leehy, M. et al., "Safety and Tolerability of Cannabidiol in Parkinson's Disease: An Open Label, Dose-Escalation Study, Cannabis and Cannabinoid Research", 2020, vol. 5, No. 4.

(56) References Cited

OTHER PUBLICATIONS

McPartland, J. et al., "Care and Feeding of the Endocannabinoid System: A Systematic Review of Potential Clinical Interventions that Upregulate the Endocannabinoid System". PLOS One, Mar. 12, 2014, vol. 9, Issue 3.

Ohlsson, Per-Ingvar, "Lacetoperoxidase, a dithionite ion dismutase" Eur. J. Biochem, 1984, vol. 142, pp. 233-238.

Polito, Vince, "A systematic study of microdosing psychedelics", PLOS, vol. 14(2), p. 1-26, 2019.

Shapiro, L., "Children, but Linked to Side Effects Analysis: Clinicians should consider adverse effects before treatment", Dravet Syndrome News, Aug. 30, 2022.

Sinha V.R. et al., "Permeation Enhancers for Transdermal Drug Delivery", Drug Development and Industrial Pharmacy, vol. 26, p. 1131-1140, 2000.

Taylor, L. "A Phase I, Randomized, Double-Blind, Placebo-Controlled, Single Ascending Dose, Multiple Dose and Food Effect Trial of the Safety, Tolerability and Pharmacokinetics of Highly Purified Cannabidiol in Healthy Subjects", CNS Drugs, 2018, vol. 32, pp. 1053-1067.

Valenta, Claudia et al., "The use of polymers for dermal and transdermal delivery" European Journal of Pharmaceutics and Biopharmaceutics, pp. 279-289, vol. 58 (2), 2004.

Touitou et al., Transdermal delivery of tetrahydrocannabinol.Int J Pharmaceutics. Apr. 1988;43(1-2):9-15.4.

Communication pursuant to Article 94(3) EPC for European Application No. 20793917.4 dated Jun. 25, 2024.

English Translation of Japanese Patent Application 2011505382 filed Dec. 1, 2008.

International Preliminary Report on Patentability for International Application No. PCT/US2020/054070 dated Apr. 5, 2022.

International Search Report and Written Opinion for International Application No. PCT/US2020/054070 dated Jan. 1, 2021.

Office Action for Japanese Patent Application No. 2022-520408 issued on Sep. 24, 2024.

Second Office Action for Chinese Patent Application No. 20280077942.3 issued on Sep. 19, 2024.

Beal, J. E. et al., Dronabinol as a Treatment for Anorexia Associated with Weight Loss in Patients with AIDS' Journal of Pain and Symptom Management, 1995, vol. 10, pp. 89-97.

Office Action for Australian Patent Application No. 2020358869 dated Jun. 19, 2025.

Office Action for Japanese Patent Application No. 2022-520408 dated May 16, 2025 (with English translation).

\* cited by examiner

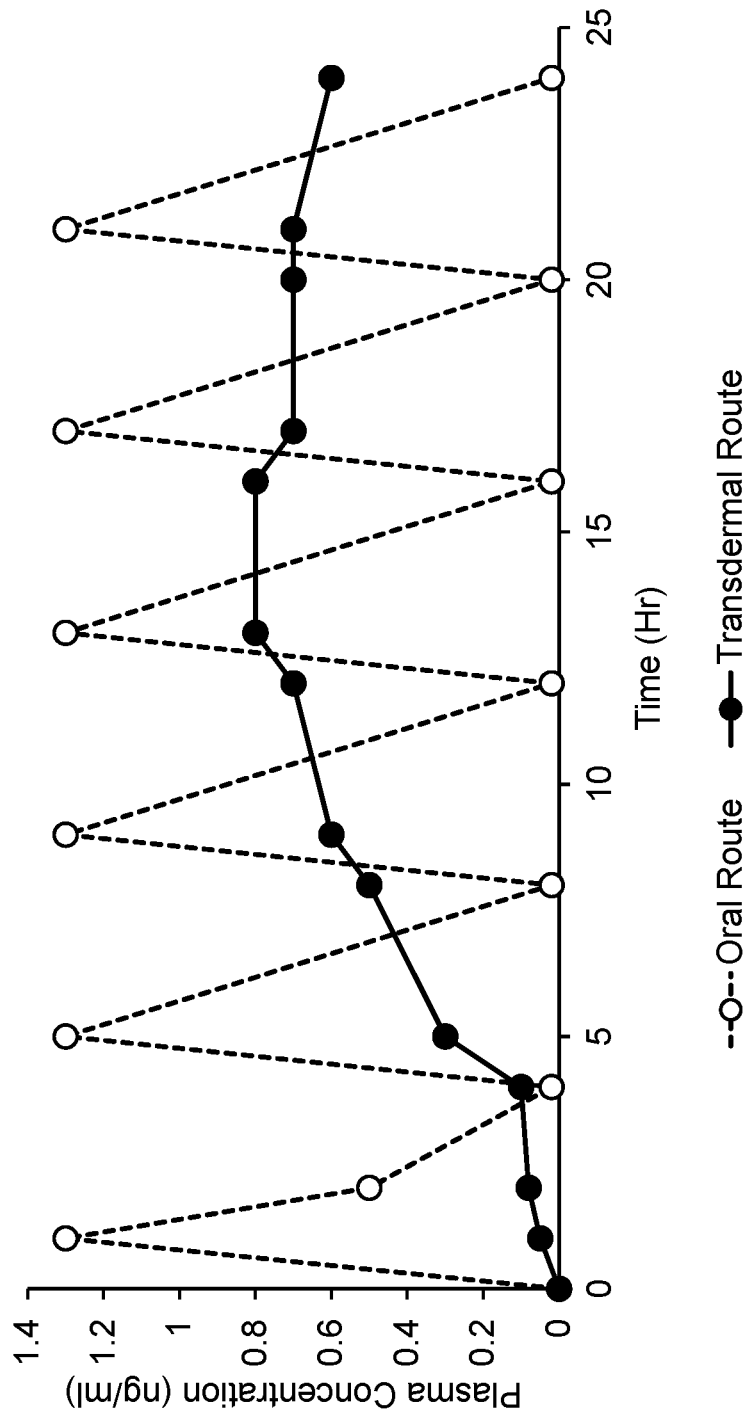

TRANSDERMAL DELIVERY OF DRONABINOL

CROSS-REFERENCE TO RELATED APPLICATIONS

This application is a continuation-in-part of, and claims the benefit of and priority to, International Application No. PCT/US2020/054070, filed on Oct. 2, 2020, which claims the benefit of U.S. Provisional Application No. 62/910,255, filed Oct. 3, 2019, both of which are incorporated by reference herein in their entirety for all purposes.

TECHNICAL FIELD

The present disclosure relates to treatment of nausea and vomiting, such as nausea and vomiting commonly experienced by patients undergoing chemotherapy.

BACKGROUND

Nausea and vomiting are the common side effects of cancer chemotherapy. Drugs such as dronabinol and $5-HT_3$ receptor antagonists are recommended for the treatment of nausea and vomiting associated with cancer chemotherapy. At times, to prevent nausea and vomiting one or more drugs can be used (See Herrsted J., et al., 2016 Updated MASCC/ ESMO Consensus Recommendations: Prevention of Nausea and Vomiting Following High Emetic Risk Chemotherapy. *Support Care Cancer.* 2017 January; 25(1): 277-288. Epub 2016 Jul. 22).

Dronabinol is a synthetic form of delta-9-tetrahydrocannbidiol (delta-9-THC) in sesame oil. Dronabinol is approved for use in treating emesis, and is available as an oral capsule (MARINOL) and as an oral solution (SYNDROS). As stated in the package insert or drug label for the oral capsule of dronabinol the drug "is indicated for the treatment of nausea and vomiting associated with cancer chemotherapy in patients who have failed to respond adequately to conventional antiemetic treatments. It is also indicated for the treatment of anorexia associated with weight loss in patients with AIDS" (See Label for NDA Marinol, Labeling, Label action date Jun. 21, 2006 accessed on Jul. 13, 2017, hereafter "Label").

Many shortcomings are associated with the dronabinol oral capsule. The first challenge is the dosage regimen. For an antiemetic effect the following dosage regimen is recommended: 1 to 3 hours before the chemotherapy a first dose of 5 $mg/m^2$ is administered orally. After chemotherapy drug is administered every 2 to 4 hours in total 4 to 6 doses per day. Depending on the clinical response, if the dose is not sufficiently effective then the dose is increased by increments of 2.5 $mg/m^2$ up to about 15 $mg/m^2$. This dosage regimen is inconvenient for patients who are already experiencing nausea and vomiting. A second challenge is that the pharmacologic response is dose related and there is inter-patient variability. A third challenge is that at maximum dose the likelihood of disturbing psychiatric symptoms increases. A fourth challenge is that after oral administration dronabinol undergoes first pass hepatic metabolism and has high lipid solubility; therefore, of the administered dose 10%-20% reaches systemic circulation. Another challenge is that at room temperature the active ingredient dronabinol is unstable is the capsules, and so the capsules are packaged in a closed container and recommended storage is in refrigerator or between 8° C.-15° C. (See FDA Label https://www.accessdata.fda.gov/drugsatfda_docs/label/2017/018651s029lbl.pdf). The dronabinol capsule is stable for only 3 months at room temperature. This is due to synthetic delta-9-THC exhibiting rapid oxidation and acid and basic degradation. Moreover, synthetic delta-9-THC also degrades more rapidly in light and at higher temperatures the degradation rate increases. Accordingly, if dronabinol capsules are not stored refrigerated and in the original container, the concentration of delta-9-THC in the capsules will decrease, potentially below the therapeutically required concentration.

Dronabinol is a synthetic form of delta-9-tetrahydrocannbidiol (delta-9-THC) in sesame oil. Previous studies have been performed with naturally derived delta-9-THC from marijuana plant *Cannabis sativa* L. However, it is difficult to extract pure delta-9-THC from a plant source, such as *sativa* L. This is caused by an adulteration of the extract by small amounts of another active cannabidiols (such as cannabinol, delta-8-THC, cannabidiol and cannabichromene) present in final product. Accordingly, the amount of THC in final extract is dependent on the extraction process which is important due to the psychoactive properties of THC, among other considerations. Alternatively, the synthetic form of delta-9-THC is developed under a more controlled procedure as opposed to the extraction process for its naturally derived counterpart. For example, synthetically produced delta-9-THC consists essentially of uncontaminated delta-9-THC that is not adulterated by the presence of other active cannabidiols. Therefore, the synthetic version of delta-9-THC is able to provide improved transdermal permeability as compared to previously published work with naturally derived delta-9-THC which demonstrates a maximum flux of 0.01 $\mu g/cm^2/hr$ through rat skin for naturally extracted delta-9-THC (U.S. Pat. No. 6,503,532).

U.S. Pat. No. 6,328,992 discloses the preparation of transdermal delivery of cannabinoids. However, the disclosure describes different cannabinoids in combination and does not describe the use of pure synthetic delta-9-THC alone. Furthermore, the '992 patent inventors describe the use of permeability enhancers which are not pharmaceutical grade and not included in U.S. Food and Drug Administration Inactive Ingredient Listing (FDA IIG). Therefore the disclosure of the '992 does not provide a composition with any pharmaceutical utility. Furthermore, the '992 patent describes the use of rat skin with 50% ethanol in receiving media for the transdermal permeability testing. However, ethanol destroys the dermis skin structure and can increase the in-vitro flux value thus providing results that are not germane to transdermal patches for pharmaceutical applications. For example, ethanol treated rat skin is almost ten time more permeable than human cadaver skin.

U.S. Pat. No. 8,449,908 provides delivery of the cumulative amount of 10000 ng THC in 96 hrs through the human cadaver skin. This amount represents the flux of 60 $ng/cm^2/hr$. The patch area can be calculated using following equation:

$$\text{In-Vitro Flux}(ng/cm^2/hr) = (Css(ng/mL) * CL(L/kg*hr) * BW(Kg))/\text{Patch Area}(cm^2)$$

$$\text{Patch Area}(cm^2) = (Css(ng/mL) * CL(L/kg*hr) * BW(kg))/\text{In-Vitro Flux}(ng/cm^2/hr) = (1.38*0.2*70*1000)/60 = 322\ cm^2$$

In order to deliver a therapeutic dosage of 5 mg/day of delta-9-THC, a transdermal formulation would need to cover at least 325 $cm^2$ surface area of the patient's skin. This is an impractical patch size for any transdermal drug delivery system (TDDS).

Therefore, there is a need for an improved drug delivery system of dronabinol which can overcome above stated drawbacks associated with oral administration and naturally derived delta-9-THC. As provided herein, transdermal delivery of dronabinol comprising synthetic delta-9-THC can address the challenges associated with oral drug delivery.

BRIEF SUMMARY

The following aspects and embodiments thereof described and illustrated below are meant to be exemplary and illustrative, not limiting in scope.

In one aspect, a pharmaceutical composition comprising dronabinol in a dosage form for transdermal delivery is provided.

In an embodiment, the pharmaceutical composition comprises no additional antiemetic drug.

In an embodiment, dronabinol is in a form selected from the group consisting of co-crystals, amorphous, coated, crystalline, a salt, an isomer, a solid solution, a prodrug, an analog, a derivative, a metabolite, a solution, synthetic, an ethanol solution, and a naturally derived delta-9-tetrahydrocannabinol.

In an embodiment, dronabinol is in the composition at between about 0.01%-95% w/w or between about 0.01%-95% w/v.

In an embodiment, dronabinol is selected from a group consisting of amorphous dronabinol, crystalline dronabinol, co-crystals of dronabinol, coated dronabinol, and ethanolic solution of dronabinol in the range of 0.01%-95% w/w or w/v.

In an embodiment, dronabinol is in a salt form.

In an embodiment, the composition is formulated as transdermal liquid formulation, transdermal semisolid formulation and/or transdermal polymer matrix formulation.

In an embodiment, a carrier or an ingredient in effective amount either alone or in combinations thereof is included in the composition. In an embodiment, the carrier or ingredient is selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, and oxidants.

In an embodiment, the carrier or ingredient is in the composition in a range of between about 0.01%-95% w/w or w/v.

In an embodiment, the pharmaceutical composition is formulated as a transdermal patch.

In an embodiment, the transdermal patch is selected from the group consisting of a reservoir patch, a micro-reservoir patch, a matrix patch, a pressure sensitive adhesive patch, and an extended release transdermal film.

In an embodiment, the pharmaceutical composition is formulated as microneedles.

In an embodiment, the microneedles are formulated as a transdermal patch.

In an embodiment, a method for the treatment and/or prevention and/or control of nausea and/or vomiting associated with cancer chemotherapy comprises selecting a patient in need of treatment and/or prevention and/or control of nausea and/or vomiting associated with cancer chemotherapy; and topically applying or instructing to topically apply the pharmaceutical composition as described herein, wherein the topically applying is performed at least once in a day.

In an embodiment, the composition is a liquid formulation and/or a semisolid formulation, wherein the topically applying is done two to six times in a day, once in a day, once in two days, once in three days, once in four days, once in five days, once in six days, once in a week.

In an embodiment, the composition is topically applied once in two days, once in three days, once in four days, once in five days, once in six days, once in a week, or once in ten days.

In an embodiment, topically applying provides a constant rate of delivery of the active components of the transdermal patch over a time period.

In an embodiment, topically applying provides a steady absorption rate of dronabinol over a time period.

In an embodiment, topically applying achieves a constant blood serum level of dronabinol over a time period.

In an embodiment, topically applying achieves a reduced variability in blood serum level of dronabinol over a time period relative to oral administration of a dronabinol over the time period.

In an embodiment, topically applying achieves a plasma concentration of dronabinol in a therapeutic range over a period of time.

In an embodiment, as method for the treatment and/or prevention and/or control of nausea and/or vomiting associated with cancer chemotherapy and/or anorexia associated with weight loss in patients with AIDS comprises selecting a patient in need of the treatment and/or prevention and/or control of nausea and/or vomiting associated with cancer chemotherapy and/or anorexia associated with weight loss in patients with AIDS; topically applying or instructing to topically apply the pharmaceutical composition described herein; wherein applying achieves topical delivery of dronabinol for the treatment and/or prevention and/or control of nausea and/or vomiting associated with cancer chemotherapy and/or anorexia associated with weight loss in patients with AIDS.

In an embodiment, the pharmaceutical composition is topically applied once in a day, once in two days, once in three days, once in four days, once in five days, once in six days, once in a week, or once in ten days.

In an embodiment, the pharmaceutical composition is topically applied two to six times in a day, once in a day, once in two days, once in three days, once in four days, once in five days, once in six days, once in a week.

In an embodiment, the pharmaceutical composition is a liquid formulation or a semisolid formulation.

In an embodiment, the pharmaceutical composition is a transdermal delivery system.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

BRIEF DESCRIPTION OF THE DRAWINGS

FIG. 1 is a graph showing the plasma concentration of a drug as a function of time, in hours, when delivered via the oral rout (open circles) or the transdermal route (closed circles).

DETAILED DESCRIPTION

In transdermal drug delivery, a transdermal patch or transdermal composition is applied topically to the skin surface. Throughout the duration of topical application of a transdermal patch or transdermal composition drug is continuously released and delivered through the intact skin (via transcellular, intercellular and trans-appendageal routes) to achieve systemic effect. Therefore, once applied the transdermal composition or transdermal patch can deliver drug into systemic circulation throughout the day or even for more than one day depending on the duration of its application, which can be up to a week or longer.

Transdermal delivery can reduce the dosing frequency of dronabinol which is currently administered orally 4-6 times a day. Through transdermal delivery, transdermal compositions or transdermal formulations or transdermal patch of dronabinol can be applied topically to skin thereby delivering the drug throughout the duration of topical application. Depending on the requirement, duration of topical application and can be once in day, once in two days, once in three days, once in four days, once in five days, once in six days, once in a week. Therefore, transdermal delivery can overcome the multiple dose regimen of oral delivery by reducing the dosing frequency.

Moreover, in transdermal drug delivery drug is delivered slowly and continuously throughout the duration of topical application hence there are no peaks and troughs in drug plasma concentration which are associated with multiple dose administration in a day. Therefore, by transdermal delivery of dronabinol patients can have the therapeutic effect of the drug for extended period of time without drastic changes in drug plasma concentration.

In transdermal delivery drug is delivered into systemic circulation through the skin, it escapes the first pass hepatic metabolism therefore to achieve the desired therapeutic activity less drug is required, resulting into less adverse effects or side effects. Dronabinol has high lipid solubility and after oral administration undergoes hepatic first pass metabolism therefore of the administered dose 10%-20% reaches systemic circulation hence, as compared to oral dose with transdermal delivery small dose of dronabinol can give the desired therapeutic effects and can also overcome the disturbing psychiatric symptoms associated with high dose.

Also, the transdermal delta-9-THC delivery described herein provides almost 10 times more in-vitro permeability through human cadaver skin using FDA IIG database for approved drug products listed ingredients, as compared to previous systems.

For example, according to FDA labels for Marinol (dronabinol capsule) were given to healthy volunteers (n=34; 20-25 years) twice a day under fasted condition, the following pharmacokinetic (PK) parameters were found (see Label).

TABLE 1

Summary of Marinol ® PK parameters

| BID | Mean (S.D.) PK Parameters Value | | |
|---|---|---|---|
| Dose (mg) | $C_{max}$ ng/ml | Median $T_{max}$ (range) hr | AUC (0-12) ng * hr/mL |
| 2.5 | 1.32 (0.62) | 1.00 (0.50-4.00) | 2.88 (1.57) |
| 5 | 2.96 (1.81) | 2.50 (0.50-4.00) | 6.16 (1.85) |
| 10 | 7.88 (4.54) | 1.50 (0.50-3.50) | 15.2 (5.52) |

Additionally, according to the PK parameters, the maximum plasma concentration for oral delivery of 5 mg/day by dronabinol capsule is 1.32 ng/ml and for oral delivery of 20 mg/day the maximum plasma concentration is 7.88 ng/mL. The oral delivery PK values demonstrate a peak and valley in plasma concentration over time. In contrast to oral delivery, transdermal drug delivery delivers the drug molecule at predetermined rate and maintains constant average plasma concentration over time (FIG. 1).

The average plasma concentration is calculated in the following manner:

Average Plasma Concentration for 5 mg/day=
$AUC_{(0-t)}/t$=2.88/12=0.24 ng/ml 20
mg/day=15.2/12=1.27 ng/ml Therefore, transdermal drug delivery systems (TDDS) are calculated to deliver delta-9-THC, at average plasma concentrations of 0.24-1.27 ng/mL.

For the prevention of nausea and vomiting, the oral route is often not the most convenient. Patients are already experiencing nausea and vomiting and if they vomit shortly after the drug administration uncertainty remains whether the dose was absorbed or is vomited. On the other hand, transdermally dronabinol will be delivered through the skin which completely eliminates these kinds of uncertainties.

Moreover, there are various additional side effects, such as Central Nervous System (CNS) side effects, related to oral dronabinol capsule administration. The side effects are dose related and therefore patients receiving the oral dosage require close monitoring so that the dosage can be adjusted and reduced as needed.

Alternatively, the TDDS systems provided herein provide constant drug delivery at a predetermined and defined input rate. Therefore, the currently provided TDDS systems provide a constant average plasma concentration due to constant input rates and do not exhibit PK peaks and valleys in plasma concentration associated with orally delivered delta-9-THC. Accordingly, the currently provided TDDS systems are also not as likely to cause CNS side effects as compared to the orally delivered counterparts. For example, adverse effects of delta-9-THC are not induced with a dosage of 7 mg/m² of delta-9-THC as shown in the following examples. Dosages greater than 7 mg/m² of delta-9-THC had no CINV effect and had more side effects.

Furthermore, oral dosages must be divided by being provided 4 to 6 times per day instead of taking once a day in order to avoid adverse effects. Additionally, oral dosage undergoes first pass metabolism and only 10-20% of the oral dose becomes available in plasma, resulting an inefficient delivery method and a large loss of the active pharmaceutical. Moreover, in order to achieve therapeutic effect form any drug molecule, the drug should have continuous delivery to achieve steady state plasma concentration or a plasma concentration in therapeutic window (between minimum and maximum therapeutic effective concentration). Therefore, the TDDS systems for delta-9-THC provided herein address long felt and unmet needs in the field of cannabidiol based pharmaceuticals.

Also, transdermal delivery is easy, noninvasive and convenient. Administration of transdermal patch or transdermal composition does not require medical supervision as patients can topically apply the transdermal patch or transdermal composition themselves.

With respect to dronabinol it is expected that interpatient variability in pharmacologic response will be less with the transdermal delivery as drug plasma concentration can be controlled by controlling the rate of drug delivery from transdermal composition or transdermal patch. Alpha half-life of dronabinol is about 4 hours, by oral administration it gets rapidly metabolized in the body. In contrast, with transdermal delivery small amount of dronabinol can be delivered for longer duration than oral administration. Transdermal formulations of dronabinol also provide more abuse deterrence than immediate release dosage forms.

Moreover, in case of any adverse effect, side effect or emergency transdermal delivery gives the liberty to terminate the therapy anytime by taking off the transdermal patch or transdermal composition from skin.

As per above stated reasons for the prevention of nausea and vomiting associated with cancer chemotherapy transdermal delivery can provide patient friendly, simplified and convenient therapeutic regimen over traditional delivery systems. Transdermal delivery can reduce the dosing frequency of dronabinol. Depending on the necessity, dosing frequency can be once in a day, once in two days, once in three days, once in four days, once in five days, once in six days, once in a week.

For the prevention of nausea and vomiting associated with cancer chemotherapy patients are prescribed with a variety of different drugs, some of which are administered multiple times a day. By formulating the antiemetic drug(s) in a transdermal patch or transdermal composition provides a much-simplified dosage regimen to patients who are already weak and tired due to chemotherapy. Depending on the necessity, dosing frequency of the transdermal patch or transdermal composition containing the drug can be once in a day, once in two days, once in three days, once in four days, once in five days, once in six days, once in a week. It would be a great addition to the patient compliance.

Dronabinol is an unstable drug. Stability of dronabinol can be improved by preparation of dronabinol's co crystals, coating the dronabinol, dronabinol's crystals, amorphous form, and/or inert substances, and the like.

Transdermal drug delivery composition, that in one embodiment, are in the form of a transdermal patch or delivery system comprising dronabinol are contemplated . . . Transdermal delivery can provide drug plasma concentration at predetermined rate for a predetermined period of time with a simplified therapeutic regimen by decreasing dosing frequency. Preferably, without any limitation dronabinol is selected from group such as dronabinol's co crystals, dronabinol's amorphous form, coated dronabinol, dronabinol's crystalline form.

As used herein, "dronabinol" refers to all forms of dronabinol either alone or in combinations thereof, for example, in following forms but not limited to such as free base or salts or isomers or amorphous or crystalline or co-crystals or solid solution or prodrugs or analogs or derivatives or metabolites or coated form or natural extract of delta-9-tetrahydrocannabinol or synthetic delta-9-tetrahydrocannabinol, solution of dronabinol. For example, dronabinol's free form or its salts or its isomers or its amorphous form or its crystalline form or its co crystals or its solid solution or its prodrugs or its analogs or its derivatives or its metabolites or its coated form or natural extract of delta-9-tetrahydrocannabinol or synthetic delta-9-tetrahydrocannabinol, ethanolic solution of dronabinol. Dronabinol may be in the form of a pharmaceutically acceptable salt, such as an acid addition salt or a base salt, or a solvate thereof, including a hydrate thereof. Suitable acid addition salts are formed from acids which form non-toxic salts.

Chemical Name: (6aR-trans)-6a,7,8,10a-tetrahydro-6,6,9-trimethyl-3-pentyl-6H-dibenzo[b,d]pyran-1-ol Empirical Formula: $C_{21}H_{30}O_2$ Molecular weight: 314.47

Structure: Formula 1

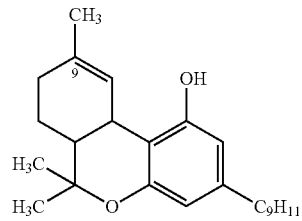

Formula 1

Dronabinol is synthetic delta-9-tetrahydrocannabinol. Delta-9-tetrahydrocannabinol is a natural component, present in *Cannabis sativa* L In embodiments of the disclosure, without any limitation, a preferable form of dronabinol is selected from group such as dronabinol co-crystals, dronabinol amorphous form, coated dronabinol, dronabinol crystalline form. Dronabinol's co-crystals, coated dronabinol, dronabinol's crystalline form may be prepared.

Amorphous forms of the drug do not have a definite structure. An amorphous form of the drug has higher solubility as compared to a crystalline form. Different techniques and methods are used to make amorphous form of drugs.

As stated in regulatory classification of pharmaceutical co-crystals guidance for industry "Co-crystals are crystalline materials composed of two or more different molecules, typically drug and co-crystal formers ("coformers"), in the same crystal lattice" (See U.S. Department of Health and Human Services Food and Drug Administration Center for Drug Evaluation and Research (CDER), Regulatory Classification of Pharmaceutical Co-Crystals Guidance for Industry Draft Guidance, Pharmaceutical Quality/CMC Revision 1, August 2016 https://www.fda.gov/downloads/Drugs/Guidances/UCM516813.pdf, accessed on Jul. 12, 2017). Different methods are available for the preparation of co-crystals. Each drug has distinct chemical structure and physicochemical properties therefore, it is difficult to predict the success rate of co-crystallization reaction. Studies under various experimental conditions are done to determine an approach to form co-crystals of drug (See Nate Schultheiss, Ann Newman. Pharmaceutical Cocrystals and their Physicochemical Properties. Cryst Growth Des. 2009 Jun. 3; 9 (6): 2950-2967).

Coating of the drug can be done with polymer or other excipients. Different techniques are used for the coating of drug. Stability of the drug can also be increased by encapsulation.

As used herein, the term "pharmaceutically acceptable salts" includes acid addition salts or addition salts of free bases. The term "pharmaceutically acceptable salts" of the dronabinol within its scope all the possible isomers and their mixtures, and any pharmaceutically acceptable metabolite, bio-precursor and/or pro-drug, such as, for example, a compound which has a structural formula different from the one of the compounds of the disclosure, and yet is directly or indirectly converted in vivo into a compound of the disclosure, upon administration to a subject, such as a mammal, particularly a human being.

In one embodiment, dronabinol is incorporated into the transdermal system in the form of a pharmaceutically acceptable salt form, either as a single salt, as combinations of salts, or as a combination of the base form and one or more salt forms. Examples of the various forms of dronabinol include but not limited to such as free base, salts, racemic form, isomers, amorphous, crystalline, co-crystals, solid solution, prodrugs, analogs, derivatives, metabolites, solutions, hydrates. Therapeutic agents may be in the form of a pharmaceutically acceptable salt, such as an acid addition salt or a base salt, or a solvate thereof, including a hydrate thereof. Suitable acid addition salts are formed from acids which form non-toxic salts and without any limitation examples are acetate, hydrochloride, hydrobromide, hydroiodide, sulphate, bisulphate, nitrate, phosphate, hydrogen phosphate, sodium phosphate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and without any limitation examples are the sodium, potassium, aluminum, calcium, magnesium, zinc and diethanolamine salts.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is a human.

As used herein, the term "agent" refers to any molecule, compound, methodology and/or substance for use in the prevention, treatment, management and/or diagnosis of a disease or condition.

As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof.

In certain embodiments, the terms "therapy" and "therapies" refer to small molecule therapy.

The term "derivative" or "derivatized" as used herein includes chemical modification of a compound of the disclosure, or pharmaceutically acceptable salts thereof or mixtures thereof. That is, a "derivative" may be a functional equivalent of a compound of the disclosure, which is capable of inducing the improved pharmacological functional activity in a given subject.

As used herein, the terms "composition" and "formulation" are used interchangeably.

As used herein, the term "topical delivery" means delivery of drug into systemic circulation through the skin.

Transdermal Compositions

According to certain embodiments, transdermal compositions described herein are for the prevention and/or treatment of nausea and/or vomiting associated with cancer chemotherapy.

According to certain embodiments described herein, the pharmaceutical composition or transdermal formulation contains dronabinol in a form selected from a group such as co-crystals, amorphous form, crystalline form, its coated form, its solution, and its salts which can be anhydrous and/or hydrous alone or in combinations thereof. More preferably the transdermal formulation may include dronabinol selected from following forms: amorphous or co-crystals or crystalline or coated or its ethanolic solution either alone or in combination of thereof.

One embodiment of the present disclosure can be a transdermal drug delivery system which may include without any limitation a transdermal formulation, a transdermal patch, a topical formulation, microneedles, iontophoresis, or a metered dose transdermal spray.

Transdermal formulation which includes liquids for example without any limitation like solutions, suspensions, dispersions, emulsion. Transdermal formulation includes semisolids for example without any limitations like gels, ointments, emulsions, creams, suspension, paste, lotion, balm. Liquid formulation and/or gel formulation incorporated in transdermal patch is preferred. Transdermal formulations which include a polymer matrix can be, without any limitation, an adhesive matrix or a non-adhesive matrix.

Without any limitation, transdermal patch may include all transdermal drug delivery systems stated in art preferably but not limited to reservoir patch, matrix patch, bilayer matrix patch, multilayer matrix patch, microreservoir patch, adhesive systems, transdermally applicable tape and other.

In certain embodiments of the present disclosure, a transdermal patch comprises dronabinol contained in a reservoir or a matrix, and an adhesive which allows the transdermal patch to adhere to the skin, allowing the passage of the dronabinol from the transdermal patch through the skin of the patient. The transdermal delivery system can be occlusive, semi-occlusive or non-occlusive, and can be adhesive or non-adhesive.

In some embodiments, the transdermal patches provide for a constant rate of delivery of the active components of the transdermal patch over a predetermined time period. In some embodiments, the predetermined time period is about 24 hours, 48 hours, 72 hours, 96 hours, 120 hours, 144 hours, 7 days, 8 to 13 days, two weeks, or 15 days.

In yet further embodiments, the transdermal patches described herein provide a steady absorption rate of the active components of the transdermal patches by the patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a constant blood serum level of the active components of the transdermal patches in a patient over a predetermined time. In some embodiments, the predetermined time period is about 24 hours, 48 hours, 72 hours, 96 hours, 120 hours, 144 hours, 7 days, 8 to 13 days, two weeks, or 15 days.

In yet further embodiments, the transdermal patches described herein provide a plasma concentration of the active components of the transdermal patches in a therapeutic range in a patient over a predetermined time. In some embodiments, the predetermined time period is about 24 hours, 48 hours, 72 hours, 96 hours, 120 hours, 144 hours, 7 days, 8 to 13 days, two weeks, or 15 days.

In yet further embodiments, the transdermal patches described herein allow for reduced variability in dosage of active components in a patient over a predetermined time. In some embodiments, the predetermined time period is about 24 hours, 48 hours, 72 hours, 96 hours, 120 hours, 144 hours, 7 days, 8 to 13 days, two weeks, or 15 days.

The topical formulation stated in the art which include, for example without any limitation, semisolids such as ointment, cream, emulsion, micro emulsion, nano emulsion, paste, balms, gels, lotions, mousses. Liquids such as solutions, suspensions, micro suspension, nano suspension, dispersions, nano dispersion etc. Sprays, aerosols, magma, etc. The topical formulation comprising dronabinol can be topically applied to the skin surface for transdermal delivery of dronabinol.

The transdermal formulation and/or topical formulation of some embodiments of the present disclosure may include carriers or ingredients in effective amount either alone or in combinations thereof without any limitation to the following carriers or ingredients such as solvents, gelling agents, polymers, biodegradable polymers, penetration enhancers, emollients, skin irritation reducing agents, buffering agents, pH stabilizers, solubilizers, suspending agents, dispersing agents, stabilizers, plasticizers, tackifiers, surfactants, volatile chemicals, antioxidants, oxidants, chelating agents, complexing agents, diluents, excipients, material to prepare patch, material to prepare a matrix patch or a reservoir patch.

Dronabinol may be dissolved, suspended, dispersed or uniformly mixed in the above stated single carrier, mixture of carriers and combinations of carrier.

The desired optimum transdermal and/or topical formulation of dronabinol may comprise without any limitation to following carriers as stated from Example 1 to Example 11 either alone or in combinations thereof.

EXAMPLES

Example 1

A transdermal formulation and/or topical formulation comprises solvents, alone or in combinations thereof, including but not limited to alcohol C1-C20 such as but not limited to (methanol, ethanol, isopropyl alcohol, butanol, propanol etc.), polyhydric alcohols, glycols such as but not limited to (propylene glycol, polyethylene glycol, dipropylene glycol, hexylene glycol, butyene glycol, glycerine etc.), derivative of glycols, pyrrolidone such as but not limited to (N methyl 2-pyrrolidone, 2-pyrrolidone etc.), sulfoxides such as but not limited to (dimethyl sulfoxide, decymethylsulfoxide etc), dimethylisosorbide, mineral oils, vegetable oils, water, polar solvents, semi polar solvents, non-polar solvents, volatile chemicals which can be used to make matrix patch such as but not limited to (ethanol, propanol, ethyl acetate, acetone, methanol, dichloromethane, chloroform, toluene, IPA), acids such as but not limited to acetic acid, lactic acid, levulinic acid, fatty acids, bases and others. The mentioned solvents are, in an embodiment, in the range of 0.01%-95% w/w or w/v.

Example 2

A transdermal formulation and/or topical formulation comprises gelling agents and/or thickening and/or suspending agents, alone or in combinations, including but not limited to natural polymers, polysaccharides and its derivatives such as but not limited to (agar, alginic acid and derivatives, cassia tora, collagen, gelatin, gellum gum, guar gum, pectin, potassium, or sodium carageenan, tragacanth, xantham, gum copal, chitosan, resin etc.), semisynthetic polymers and its derivatives such as without any limitation to cellulose and its derivatives (methylcellulose, ethyl cellulose, carboxymethyl cellulose, hydroxylpropyl cellulose, hydroxylpropylmethyl cellulose etc.), synthetic polymers and its derivatives such as without any limitation to carboxyvinyl polymers or carbomers (carbopol 940, carbopol 934, carbopol 971p NF), polyethylene, and its copolymers etc, clays such as but not limited to (silicates, bentonite), silicon dioxide, polyvinyl alcohol, acrylic polymers (eudragit), acrylic acid esters, polyacrylate copolymers, polyacrylamide, polyvinyl pyrrolidone homopolymer and polyvinyl pyrrolidone copolymers such as but not limited to (PVP, Kollidon 30, Poloxamer), isobutylene, ethyl vinyl acetate copolymers, natural rubber, synthetic rubber, pressure sensitive adhesives such as silicone polymers such as but not limited to (bio-psa 4302, bio-psa 4202 etc.,), acrylic pressure sensitive adhesives such as but not limited to (DURO-TAK 87-2156, DURO-TAK 387-2287, etc.), polyisobutylene such as but not limited to (polyisobutylene low molecular weight, polyisobutylene medium molecular weight, polyisobutylene 35000 mw, etc), acrylic copolymers, rubber based adhesives, hot melt adhesives, styrene-butadiene copolymers, bentonite, all water and/or organic solvent swellable polymers, etc. The mentioned agents are, in an embodiment, in the range of 0.1% 70% w/w or w/v.

Example 3

The transdermal formulation and/or topical formulation of the disclosure may comprise permeation enhancers known to those skilled in the art either alone or in combination thereof without any limitation to the following, such as sulfoxides, and similar chemicals such as but not limited to (dimethylsulfoxide, dimethylacetamide, dimethylformamide, decymethylsulfoxide, dimethylisosorbide etc), azone, pyrrolidones such as but not limited to (N-methyl-2-pyrrolidone, 2-pyrrolidon etc.), esters, fatty acid esters such as but not limited to (propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate etc.), fatty acids such as but not limited to (capric acid, caprylic acid, lauric acid, oleic acid, myristic acid, linoleic acid, stearic acid, palmitic acid etc.), alcohols, fatty alcohols and glycols such as but not limited to (oleyl alcohol, nathanol, dodecanol, propylene glycol, glycerol etc.), ethers alcohol such as but not limited to (diethylene glycol monoethyl ether), urea, triglycerides such as but not limited to triacetin, polyoxyethylene fatty alcohol ethers, polyoxyethylene fatty acid esters, esters of fatty alcohols, essential oils, surfactant type enhancers such as but not limited to (brij, sodium lauryl sulfate, tween, polysorbate), terpene, terpenoids and all penetration or permeation enhancers referred in the book "Percutaneous Penetration Enhancers" (Eric W. Smith, Howard I. Maibach, 2005. Nov, CRC press). The mentioned agents are, in an embodiment, in the range of 0.01%-95% w/w or w/v.

Example 4

A transdermal formulation and/or topical formulation comprises plasticizers alone or in combination thereof, including without any limitation glycerol and its esters, phosphate esters, glycol derivatives, sugar alcohols, sebacic acid esters, citric acid esters, tartaric acid esters, adipate, phthalic acid esters, triacetin, oleic acid esters and all the plasticizers which can be used in transdermal drug delivery system referred in the book "Handbook of Plasticizers" (George Wypych, 2004, Chem Tec Publishing). The mentioned agents are, in an embodiment, in the range of 0.01%-95% w/w or w/v.

Example 5

A transdermal formulation and/or topical formulation comprises emollients, humectants, and/or skin irritation reducing agents either alone or in combinations thereof without any limitation to following like petrolatum, lanolin, mineral oil, dimethicone, zinc oxide, glycerin, propylene glycol and others. The mentioned agents are, in an embodiment, in the range of 0.01%-95% w/w or w/v.

Example 6

A transdermal formulation and/or topical formulation comprises solubilizers, surfactants, emulsifying agents, dispersing agents alone or in combination thereof without any limitation to following: surfactants, including anionic, cationic, nonionic and amphoteric surfactants, such as the sorbitan oleates under the trade name SPAN such as but not limited to SPAN 80, SPAN 20 etc. and the polysorbates such as but not limited to Polysorbate 20, Polysorbate 40, Polysorbate 60,Polysorbate 80 etc., propylene glycol monocaprylate type I, propylene glycol monocaprylate type II, propylene glycol dicaprylate, medium chain triglycerides, propylene glycol monolaurate type II, linoleoyl polyoxyl-6 glycerides, oleoyl-polyoxyl-6-glycerides, lauroyl polyoxyl-6-gylcerides, polyglyceryl-3-dioleate, diethylene glycol monoethyl ether, propylene glycol monolaurate type I, polyglyceryl-3-dioleate, caprylocaproyl polyoxyl-8 glycerides etc, cyclodextrins and others. The mentioned agents are, in an embodiment, in the range of 0.01% 95% w/w or w/v.

Example 7

Different techniques and ingredients can be used to increase the stability and/or solubility of dronabinol in the formulation such as without any limitation coating, encapsulation, microencapsulation, nanoencapsulation, lyophilization, chelating agents, complexing agents, etc.

Example 8

A transdermal formulation and/or topical formulation comprises auxiliary pH buffering agents and pH stabilizers and similar compounds known to those skilled in the art to maintain the appropriate pH of formulation preferably in the range of 4.0-8.0 either alone or in combination thereof without any limitation to following such as phosphate buffer, acetate buffer, citrate buffer, etc., acids such as but not limited to (carboxylic acids, inorganic acids, sulfonic acids, vinylogous carboxylic acids, fatty acids, and others), base such as but not limited to (sodium hydroxide, potassium hydroxide, ammonium hydroxide, triethylamine, sodium carbonate, sodium bicarbonate) etc. The mentioned agents are, in an embodiment, in the range of 0.01%-30% w/w or w/v.

Example 9

A transdermal formulation and/or topical formulation comprises antioxidants, such as but not limited to, sodium metabisulfite, citric acid, ascorbic acid, BHA, and BHT, oxidizing agents, stabilizers, discoloring agents, preservatives and similar compounds or chemicals to provide a stable formulation. The mentioned agents are, in an embodiment, in the range of 0.01%-50% w/w or w/v.

Example 10

A transdermal formulation and/or topical formulation with dronabinol formulated in ointment and/or cream base, gels, lotions, and other topical formulations.

Example 11

Materials to make the transdermal delivery system of the disclosure in patch form known to those skilled in the art, for example, such as but not limited to reservoir patch, matrix patch, drug in adhesives, transdermal films and may include, such as but are not limited to polymers, copolymers, derivatives, backing film, release membranes, release liners, etc. either alone or in combinations thereof. Pressure sensitive adhesives (such as but not limited to silicone polymers, rubber based adhesives, acrylic polymers, acrylic copolymers, polyisobutylene, acrylic acid-isooctyl acrylate copolymer, hot melt adhesives, polybutylene etc.), backing film (such as but not limited to ethylene vinyl acetate copolymers, vinyl acetate resins, polyurethane, polyvinyl chloride, metal foils, polyester, aluminized films, polyethylene, etc.), release membrane (such as but not limited to microporous polyethylene membrane, microporous polypropylene membrane, rate controlling ethylene vinyl acetate copolymer membrane etc.), release liners (such as but not limited to siliconized polyester films, fluoropolymer coated polyester film, polyester film, siliconized polyethylene terephthalate film, etc.), tapes, etc.

The transdermal formulation and/or topical formulation and/or transdermal delivery system of the disclosure may deliver at least therapeutic effective dose of dronabinol. Therapeutic effective dronabinol dose refers to the therapeutic concentration of dronabinol in human plasma required for treating and/or preventing nausea and/or vomiting associated with chemotherapy. Furthermore, the precise therapeutic effective dose of dronabinol in the transdermal formulation or topical formulation or transdermal delivery system can be determined by those skilled in the art based on factors such as but not limited to the patient's condition etc. The transdermal formulation or topical formulation or transdermal delivery system will be available in different dosage strengths and patch sizes in order to achieve optimum therapeutic outcome based on patient's requirement.

In another embodiment, the transdermal formulation and/or topical formulation and/or transdermal delivery system of the disclosure may deliver at least therapeutic effective dose of dronabinol. Therapeutic effective dronabinol dose refers to the therapeutic concentration of dronabinol in human plasma required for treating as stated in MARINOL label "anorexia associated with weight loss in patients with AIDS" (See Label). Furthermore, the precise therapeutic effective dose of dronabinol in the transdermal formulation or topical formulation or transdermal delivery system can be determined by those skilled in the art based on factors such as but not limited to the patient's condition etc. The transdermal formulation or topical formulation or transdermal delivery system will be available in different dosage strengths and patch sizes in order to achieve optimum therapeutic outcome based on patient's requirement.

The transdermal formulation or transdermal patch of dronabinol preferably but not limited to can be applied to the skin surface in any of the following dosage regimens such as once in a day, once in two days, once in three days, once in four days, once in five days, once in six days, once in a week, once in a 8 to about 13 days, once in two weeks, once in 15 days.

Example 12

Synthetic delta-9-THC formulations for transdermal delivery (Formulation Nos. 001, 002, 006, 007, 008 and 009) were prepared by mixing ingredients as shown in Table 2:

TABLE 2

Transdermal Synthetic delta-9-THC formulations

| Ingredients | 001 (% W/V) | 002 (% W/V) | 006 (% W/V) | 007 (% W/V) | 008 (% W/V) | 009 (% W/V) |
|---|---|---|---|---|---|---|
| TP | 25 | | | | | |
| PG | 25 | 35 | 89.2 | 88.4 | 33 | 32.7 |
| Water | 20 | 20 | 9.9 | 9.9 | 33 | 32.7 |
| Ethanol | 29.5 | 44.5 | | | 33 | 32.7 |
| THC | 0.5 | 0.5 | 0.9 | 1.8 | 0.95 | 1.9 |

Abbreviations:
TP = Transcutol P;
PG = propylene glycol;
THC = tetrahydrocannabinol.

All of the components from Table 2, with the exception of the THC, were mixed together with stirring for 18 hours. Next, the THC in ethanol was added into the excipient mixture to prepare the final transdermal formulations.

The prepared transdermal formulations were then subjected to a flux measurement test as follows. Human cadaver skin, stored at −80° C., was thawed at room temperature in phosphate buffered saline (PBS), and visually inspected for defects before using in the study. Transdermal flux was then measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The donor compartment was filled with the transdermal THC formulations prepared as described above. The receptor compartment was filled with receptor medium, held at constant temperature, and constantly stirred to collect the THC as it diffuses through the skin and into receptor compartment. It is important to confirm that the receptor fluid is always in contact with the skin. The receptor compartment was emptied at 24 hr intervals for assay of delta-9-THC and replaced with fresh receptor solution. In order to maintain the sink condition in receptor compartment, it is important keep the delta-9-THC concentration in receptor compartment less than 10% of its solubility. The experimental conditions are provided in Table 3:

TABLE 3

Experimental Condition for In-vitro Permeability testing

| | |
|---|---|
| Receiving Media | De-ionized water + 0.5% Brij-O(20) + 0.01% Sodium Azide |
| Receiving Media Volume (mL) | 13 |
| Sample Volume (mL) | 13 |
| Sampling Interval (hr) | 24 |
| Franz-cell diffusion area (sqcm) | 1.76 |
| Membrane Type | Human Cadaver Skin |

Flux of THC through the human cadaver skin was measured for a minimum period of 96 Hrs (4 days) and results of the flux measurement are provided in Table 4.

TABLE 4

THC Flux Results

| | 001 | 002 | 006 | 007 | 008 | 009 |
|---|---|---|---|---|---|---|
| Total Amount of THC Permeated at 96 hrs (ng/cm$^2$) | 98700 | 154400 | 64200 | 122700 | 90900 | 102800 |
| Flux (ng/cm$^2$/hr) | 1000 | 1600 | 700 | 1300 | 950 | 1070 |
| Patch Area (cm$^2$) (5 mg/day) | 20 | 12 | 28 | 15 | 21 | 18 |

Example 13

Additional synthetic delta-9-THC formulations for transdermal delivery (Formulation Nos. 010 through 018) were prepared by mixing ingredients as shown in Table 5:

TABLE 5

Transdermal Synthetic delta-9-THC formulation nos. 010 to 018

| Ingredients | 010 (% W/V) | 011 (% W/V) | 012 (% W/V) | 013 (% W/V) | 014 (% W/V) | 015 (% W/V) | 016 (% W/V) | 017 (% W/V) | 018 (% W/V) |
|---|---|---|---|---|---|---|---|---|---|
| THC | 1.3 | 2.0 | 2.8 | 1.3 | 2.0 | 2.8 | 2.0 | 2.8 | 2.0 |
| Ethanol | 27.3 | 42.4 | 58.7 | 27.3 | 42.4 | 58.7 | 42.4 | 58.7 | 42.4 |
| PG | 64.3 | 50 | 34.6 | 71.4 | 55.6 | 38.5 | — | — | — |

TABLE 5-continued

Transdermal Synthetic delta-9-THC formulation nos. 010 to 018

| Ingredients | 010 (% W/V) | 011 (% W/V) | 012 (% W/V) | 013 (% W/V) | 014 (% W/V) | 015 (% W/V) | 016 (% W/V) | 017 (% W/V) | 018 (% W/V) |
|---|---|---|---|---|---|---|---|---|---|
| Water | 7.1 | 5.6 | 3.9 | — | — | — | — | — | — |
| Dimethyl Sulfoxide (DMSO) | — | — | — | — | — | — | 55.6 | 38.5 | 55.6 |

Abbreviations:
THC = tetrahydrocannabinol;
PG = propylene glycol.

Synthetic delta-9-THC formulations for transdermal delivery (010-018) were prepared by the same procedure described in Example 12. Flux measurement was also performed as described in Example 12. The experimental conditions are the same as provided in Table 3 of Example 12.

Flux of THC through the human cadaver skin was measured for a minimum period of 96 Hrs (4 days) and results of the flux measurement experiments are provided in Table 6.

TABLE 6

THC Flux Results

| | Formulation No. | | | | | | | | |
|---|---|---|---|---|---|---|---|---|---|
| | 010 | 011 | 012 | 013 | 014 | 015 | 016 | 017 | 018 |
| Total Amount of THC Permeated at 96 hrs (ng/cm$^2$) | 75600 (31%) | 94900 (20%) | 102800 (52%) | 54000 (33%) | 145500 (63%) | 204600 (43%) | 35200 (22%) | 35800 (1%) | 53400 (6%) |
| Flux (ng/cm$^2$/hr) | 800 | 1000 | 1070 | 600 | 1500 | 2100 | 400 | 400 | 600 |
| Patch Area (cm$^2$) (5 mg/day) | 24 | 19 | 18 | 32 | 13 | 9 | 48 | 48 | 32 |

Example 14

Additional synthetic delta-9-THC formulations for transdermal delivery (Formulation Nos. 019 to 027) were prepared by mixing ingredients as shown in Table 7.

TABLE 7

Transdermal Synthetic delta-9-THC formulation nos. 019-027

| Ingredients | 019 (% W/V) | 020 (% W/V) | 021 (% W/V) | 022 (% W/V) | 023 (% W/V) | 024 (% W/V) | 025 (% W/V) | 026 (% W/V) | 027 (% W/V) |
|---|---|---|---|---|---|---|---|---|---|
| THC | 2.0 | 2.0 | 2.0 | 2.0 | 2.0 | 2.0 | 2.0 | 2.0 | 2.0 |
| Ethanol | 42.4 | 42.4 | 42.4 | 42.4 | 42.4 | 42.4 | 42.4 | 42.4 | 42.4 |
| PG | 44.4 | 44.4 | 44.4 | 44.4 | 44.4 | 44.4 | 44.4 | 44.4 | 44.4 |
| NMP | 11.1 | | | | | | | | |
| Lauric acid | | 11.1 | | | | | | | |
| Oleic Acid | | | 11.1 | | | | | | |
| Lauryl Lactate | | | | 11.1 | | | | | |
| Oleyl Alcohol | | | | | 11.1 | | | | |
| GMO | | | | | | 11.1 | | | |

TABLE 7-continued

Transdermal Synthetic delta-9-THC formulation nos. 019-027

| Ingredients | 019 (% W/V) | 020 (% W/V) | 021 (% W/V) | 022 (% W/V) | 023 (% W/V) | 024 (% W/V) | 025 (% W/V) | 026 (% W/V) | 027 (% W/V) |
|---|---|---|---|---|---|---|---|---|---|
| Lactic Acid | | | | | | | 11.1 | | |
| HPC (Klucel ®) | | | | | | | | 11.1 | |

Abbreviations:
THC = tetrahydrocannabinol;
PG = propylene glycol;
NMP = n-methyl pyrrolidone;
GMO = glycerol monooleate;
HPC = hydroxypropyl cellulose.

Synthetic delta-9-THC formulations for transdermal delivery (019-027) were prepared by the same procedure described in Example 12. Flux measurement was also performed as described in Example 12. The experimental conditions are the same as provided in Table 3 of Example 12.

Flux of THC through the human cadaver skin was measured for a minimum period of 72 hours (3 days) and results of the flux measurement experiments are provided in Table 8.

Synthetic delta-9-THC formulations for transdermal delivery (formulation nos. 028 to 034) were prepared by the same procedure described in Example 12. Flux measurement was also performed as described in Example 12. The experimental conditions are the same as provided in Table 3 of Example 12.

Flux of THC through the human cadaver skin was measured for a minimum period of 120 hours (5 days) and results of the flux measurement experiments are provided in Table 10.

TABLE 8

THC Flux Results

| | Formulation No. | | | | | | | | |
|---|---|---|---|---|---|---|---|---|---|
| | 019 | 020 | 021 | 022 | 023 | 024 | 025 | 026 | 027 |
| Total Amount of THC Permeated at 72 hrs (ng/cm²) | 56300 (10%) | 29600 (82%) | 20500 (14%) | 5100 (29%) | 5100 (22%) | 26100 (34%) | 36400 (92%) | 31300 (19%) | 31300 (16%) |
| Flux (ng/cm²/hr) | 800 | 400 | 300 | 70 | 70 | 400 | 500 | 400 | 400 |
| Patch Area (cm²) (5 mg/day) | 24 | 48 | 64 | 276 | 276 | 48 | 38 | 48 | 48 |

Example 15

Additional synthetic delta-9-THC formulations for transdermal delivery (Formulation Nos. 028 to 034) were prepared by mixing ingredients as shown in Table 9:

TABLE 9

Transdermal Synthetic delta-9-THC formulation nos. 028 to 034

| Ingredients | 028 (% W/V) | 029 (% W/V) | 030 (% W/V) | 031 (% W/V) | 032 (% W/V) | 033 (% W/V) | 034 (% W/V) |
|---|---|---|---|---|---|---|---|
| THC | 2.0 | 2.0 | 2.0 | 2.0 | 2.0 | 2.0 | 2.0 |
| Ethanol | 42.4 | 42.4 | 42.4 | 42.4 | 42.4 | 42.4 | 42.4 |
| PG | 27.8 | 27.8 | 27.8 | 27.8 | 27.8 | 27.8 | 27.8 |
| 1,3 Butanediol | 27.8 | | | | | | |
| Dipropylene Glycol | | 27.8 | | | | | |
| Hexylene Glycol | | | 27.8 | | | | |
| PEG-400 | | | | 27.8 | | | |
| Tween-20 | | | | | 27.8 | | |
| Tween-80 | | | | | | 27.8 | |
| Span-20 | | | | | | | 27.8 |

TABLE 10

Transdermal Synthetic delta-9-THC formulations

| | Formulation Nos. | | | | | | |
|---|---|---|---|---|---|---|---|
| | 028 | 029 | 030 | 031 | 032 | 033 | 034 |
| Total Amount of THC Permeated at 120 Hrs (ng/cm$^2$) | 103400 (9%) | 86400 (17%) | 115300 (53%) | 61400 (43%) | 7400 (80%) | 30100 (137%) | 43800 (47%) |
| Flux (ng/cm$^2$/hr) | 900 | 700 | 1000 | 500 | 60 | 300 | 400 |
| Patch Area (cm$^2$) (5 mg/day) | 22 | 28 | 19 | 38 | 322 | 64 | 48 |

Example 16

Additional synthetic delta-9-THC formulations for transdermal delivery patches (Formulation Nos. 035 to 038) were prepared by mixing ingredients as shown in Table 11:

TABLE 11

Transdermal Synthetic delta-9-THC formulation nos. 035 to 038

| Ingredients | 035 (% W/W) | 036 (% W/W) | 037 (% W/W) | 038 (% W/W) |
|---|---|---|---|---|
| THC | 2.0 | 2.0 | 2.0 | 2.0 |
| PG | 27.8 | 27.8 | 27.8 | 27.8 |
| Hexylene Glycol | 27.8 | 27.8 | 27.8 | 27.8 |
| Durotak 9301 | 42.4 | | | |
| Durotak 2516 | | 42.4 | | |
| Durotak 2207 | | | 42.4 | |
| Silicone Adhesive | | | | 42.4 |

To prepare a transdermal patch containing synthetic delta-9-THC, all of the components from Table 11, with the exception of the THC, were mixed together with stirring for 18 hours. Next, the THC was added 30 minutes before spreading the formulation. The formulation was spread using a commercial benchtop spreader. Specifically, the formulation matrix is evenly spread onto an 8×14 inch sheet of release liner (such as 3M 9744) to a thickness of 0.5 mm. The sheet is then place in an oven at 100° F. for one hour to evaporate off the ethyl acetate and ethanol adhesive solvent. An opaque backing membrane (such as 3M 9730 NR film) with low permeability to oxygen, for inhibition of photo and oxidative degradation, is then carefully applied to the sheet by hand to avoid formation of bubbles and voids. A circular die (1.5 inches diameter) was used to cut patches (7 cm$^2$) for subsequent studies.

The general procedure for flux measurements of transdermal formulations in the examples above was as follows. The human cadaver skin, stored at −80° C., was thawed at room temperature in PBS, and visually inspected for defects before use. Transdermal flux was measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The general procedure for flux measurement of the transdermal adhesive patch is as follows. The release liner is peeled off the patch and the adhesive surface is applied to a piece of human cadaver skin (Example 16, Table 11 only). The transdermal patch was adhered to the skin with the patch on the side of the skin in contact with the donor compartment. The receptor compartment was filled with receptor medium, held at constant temperature, and constantly stirred to collect the THC as it diffuses from the adhered patch, through the skin and into receptor compartment. It was confirmed that the receptor fluid was always in contact with the skin. The receptor compartment was emptied at 24 hour intervals for assay of delta-9-THC and replaced with fresh receptor solution. In order to maintain the sink condition in receptor compartment, the delta-9-THC concentration in the receptor compartment was maintained at less than 10% of its solubility. The experimental conditions are the same as provided in Table 3 of Example 12.

Example 17

Synthetic delta-9-THC (THC) formulations for transdermal delivery (Formulation Nos. 040 through 042) were prepared by mixing ingredients as shown in Table 12:

TABLE 12

Transdermal Synthetic delta-9-THC formulation no. 040 to 042

| Excipients | THC—040 (Solution) | THC—041 (Solution) | THC—042 (Gel) |
|---|---|---|---|
| THC in ethanol (20% w/w) | 13.1% | 12.8% | 13.6% |
| Ethanol | 43.2% | 38.6% | 41.9% |
| Propylene Glycol | 43.7% | 38.6% | 43.4% |
| Hydramol | — | 10.0% | — |
| Klucel HF | — | — | 1.0% |

The following examples used composition THC_040 as an example for preparing a transdermal patch. The above excipients except THC were mixed together by stirring for 18 hours and then the THC in ethanol was added into the above excipient mixture.

The general procedure for flux measurement of transdermal formulation was conducted as follows. The human cadaver skin, stored at −80 C, was thawed at room temperature in PBS, and visually inspected for defects before using in the study. Transdermal flux was measured using standard Franz diffusion cells composed of a cylindrical donor compartment and a separate water jacketed cylindrical receptor compartment with the volume of 13 ml. The human cadaver skin was clamped between the two compartments with the dermis side facing toward the receptor compartment. The receptor compartment was filled with receptor medium, held at constant temperature, and constantly stirred to collect the THC as it diffuses through the skin and into receptor compartment, making sure that the receptor fluid was always in contact with the skin. The receptor compartment was emptied at 24 hr intervals for assay of delta-9-THC and replaced with fresh receptor solution. In order to maintain the sink condition in receptor compartment, the delta-9-THC concentration in receptor compartment was kept at less than 10% of its solubility. The experimental conditions were as follow:

| Experimental Condition for In-vitro Permeability testing | |
|---|---|
| Receiving Media | De-ionize water + 0.5% Brij-O(20) + 0.01% Sodium Azide |
| Receiving Media Volume (ml) | 13 |
| Sample Volume (ml) | 13 |
| Sampling Interval (hr) | 24, 48, 72, 96, 120 |
| Franz-cell diffusion area (sqcm) | 1.76 |
| Membrane Type | Human Cadaver Skin |

TABLE 13

Flux is measure for a minimum period of 120 Hrs (5 days)

|  | THC—040 | THC—041 | THC—042 |
|---|---|---|---|
| Avg Flux 0-24 hr, µg/sqcm/hr (% RSD) | 0.11 | 0.00 | 0.00 |
| Avg Flux 24-48 hr, µg/sqcm/hr (% RSD) | 0.72 (173.21) | 0.59 (62.53) | 2.16 (62.29) |
| Avg Flux 48-72 hr, µg/sqcm/hr (% RSD) | 1.55 (50.46) | 0.83 (12.42) | 2.93 (33.55) |
| Avg Flux 72-96 hr, µg/sqcm/hr (% RSD) | 2.15 (49.90) | 0.66 (39.91) | 3.03 (10.27) |
| Avg Flux 96-120 hr, µg/sqcm/hr (% RSD) | 1.66 (39.69) | 0.22 (87.14) | 2.03 (10.04) |
| Avg Flux 24-120 hr, µg/sqcm/hr (% RSD) | 1.24 (97.00) | 0.46 (40.40) | 2.03 (29.04) |

Example 18

Synthetic delta-9-THC (THC) formulations for transdermal delivery (Formulation Nos. 043 through 0048) were prepared by mixing ingredients as shown in Table 14:

TABLE 14

THC Matrix System

| Excipients | THC 043-R1 | THC 044-R1 | THC 045-R1 | THC 046 | THC 047 | THC 048 |
|---|---|---|---|---|---|---|
| THC | 4.05% | 4.05% | 4.05% | 7.81% | 7.86% | 7.79% |
| Oleic acid | — | 4.45% | — | — | — | — |
| Propylene Glycol | 17.00% | 12.55% | 12.16% | — | 14.94% | 15.19% |
| Isopropyl Palmitate | — | — | 4.46% | — | — | — |
| DMSO | — | — | — | 15.17% | — | — |
| Lactic Acid | — | — | — | 14.85% | 15.92% | 14.86% |
| GMO | — | — | — | 4.84% | 4.87% | 4.95% |
| Hydramol | — | — | — | 5.49% | 5.20% | 5.28% |
| BIO-PSA 4501 | 78.95% | 78.95% | 79.32% | — | — | — |
| DURO-TAK 9301 | — | — | — | 51.84% | 51.21% | — |
| DURO-TAK 2054 | — | — | — | — | — | 51.92% |

The above ingredients (Table 14) were blended by stirring for 18 hours and then, using a commercial benchtop spreader, the matrix was evenly spread onto an 8×14 inch sheet of release liner (such as 3M 9744) to a thickness of 0.5 mm. The sheet was then placed in an oven at 86 F for 120 min to evaporate off the ethyl acetate adhesive solvent. An opaque backing membrane (such as 3M 9730 NR film) with low permeability to oxygen to inhibit photo and oxidative degradation, was then carefully applied by hand to avoid formation of bubbles and voids. A circular die (1.5 inches diameter) was used to cut patches (1.76 sqcm) for subsequent studies. After drying, the drug adhesive matrix had a surface density of 2-30 mg/sqcm, containing THC in 5-20% w/w.

The prepared transdermal formulations were then subjected to a flux measurement test as follows. Human cadaver skin, stored at −80° C., was thawed at room temperature in phosphate buffered saline (PBS), and visually inspected for defects before using it in the study. Transdermal flux was then measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The donor compartment was filled with the transdermal THC formulations prepared as described above. The receptor compartment was filled with receptor medium, held at constant temperature, and constantly stirred to collect the THC as it diffuses through the skin and into receptor compartment, making sure that the receptor fluid was always in contact with the skin. The receptor compartment was emptied at 24 hr intervals for assay of THC and replaced with fresh receptor solution. In order to maintain the sink condition in receptor compartment, the THC concentration in receptor compartment was kept at less than 10% of its solubility. The experimental conditions are provided in Table 15:

TABLE 15

Experimental Condition for In-vitro Permeability testing

| Receiving Media | De-ionized water + 0.5% Brij-O(20) + 0.01% Sodium Azide |
|---|---|
| Receiving Media Volume (mL) | 13 |
| Sample Volume (mL) | 13 |
| Sampling Interval (hr) | 24, 48, 72, 96, 120, 144 |
| Franz-cell diffusion area (sqcm) | 1.76 |
| Membrane Type | Human Cadaver Skin |

Flux of THC through the human cadaver skin was measured for a minimum period of 144 Hrs (6 days) and results of the flux measurement are provided in Table 16.

TABLE 16

THC Flux Results

|  | THC 043-R1 | THC 044-R1 | THC 045-R1 | THC 046 | THC 047 | THC 048 |
|---|---|---|---|---|---|---|
| Avg Flux 0-24 hr, µg/sqcm/hr (% RSD) | 0.00 | 0.28 (173.21) | 0.00 | 0.00 | 0.00 | N/A |
| Avg Flux 24-48 hr, µg/sqcm/hr (% RSD) | 0.00 | 1.01 (16.39) | 0.00 | 0.00 | 0.00 | N/A |
| Avg Flux 48-72 hr, µg/sqcm/hr (% RSD) | 0.00 | 0.96 (12.86) | 0.52 (82.26) | 0.00 | 0.00 | N/A |
| Avg Flux 72-96 hr, µg/sqcm/hr (% RSD) | 0.00 | 1.07 (13.81) | 0.84 (2.82) | 0.00 | 0.00 | N/A |
| Avg Flux 96-120 hr, µg/sqcm/hr (% RSD) | 0.00 | 1.22 (15.51) | 0.94 (2.75) | 0.00 | 0.00 | N/A |
| Avg Flux 120-144 hr, µg/sqcm/hr (% RSD) | 0.00 | 1.03 (12.46) | 0.56 (86.67) | 0.00 | 0.00 | N/A |
| Avg Flux 24-144 hr, µg/sqcm/hr (% RSD) | 0.00 | 0.93 (21.54) | 0.43 (33.55) | 0.00 | 0.00 | N/A |

Example 19

The effect of gelling agents and their concentration on the permeation of THC through human cadaver skin. THC gel formulation can be gelled by gelling agents including but not limited to, natural polymers such as natural polymers, polysaccharides and its derivatives such as but not limited to (agar, alginic acid and derivatives, cassia tora, collagen, gelatin, gellum gum, guar gum, pectin, potassium or sodium carrageenan, tragacanth, xanthum gum, copal, starch, chitosan, resin etc.), synthetic polymers and its derivatives such as without any limitation to carboxyvinyl polymers or carbomers (carbopol 940, carbopol 934, carbopol 971), polyethylene and its co-polymers etc. clays such as silicate etc. polyvinyl alcohol, polyacrylamide, polyvinyl pyrrolidone homopolymer and polyvinyl pyyrolidone copolymers (PVP, Poloxamer), acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, as well as pressure sensitive adhesive based on silicone, or "hot-melt adhesive". In addition, other than human cadaver skin, clobazam can be evaluated with other artificial membranes including but not limited to cellulose membrane, silicone membranes (polydimethylsiloxane), liposome coated membranes, solid-supported liquid membranes, lecithin organogel membrane and other. Besides the gel formulation of clobazam, other dosage forms including but not limited to ointment, creams, emulsion, liposomes, etc. may be used.

Example 20

The effect of enhancers or solubilizers on the flux of clobazam through human cadaver skin was evaluated. The desire optimum composition of clobazam gel formulation contained dimethylsulfoxide (DMSO), dimethylisosorbide (DMI), Lactic acid, Tween-20, highly purified diethylene glycol monoethyl ether (Transcutol P), dipropylene glycol, polyethylene glycol-400, propylene glycol (PG), Hexylene Glycol (HG), Lauroglycol-90. Apart from above mentioned enhancers and/or solubilizers, the clobazam transdermal delivery can be influenced by enhancers and/or solubilizers including but not limited water, sulfoxides, and similar as but not limited to (dimethylsulfoxide, dimethylacetamide, chemicals such dimethylformamide, decylmethylsulfoxide, dimethylisosorbide etc), azone, pyrrolidones such as but not limited to (N-methyl-2-pyrrolidone, 2-pyrrolidon etc), esters such as but not limited to (Propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate etc), fatty acids such as but not limited to (capric acid, caprylic acid, lauric acid, oleic acid, myristic acid, linoleic acid, stearic acid, palmitic acid etc), alcohols, fatty alcohols and glycols such as but not limited to (oleyl alcohol, nathanol, dodecanol, propylene glycol, glycerol etc), ethers such as but not limited to (diethylene glycol monoethyl ether), urea, polyoxyethylene fatty alcohol ethers, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid diethanolamine, essential oils, terpene and terpenoids such as but not limited to (terpineol, limonene, thymol, cineole etc), surfactant type enhancers (polysorbate 80, polysorbate 20 etc.), liposomes, niosomes, transferomes, ethanosomes, polysorbate such as but not limited to (polysorbate 20, polysorbate 40, polysorbate 60, polysorbate 80 etc), span such as but not limited to (span 80, span 20 etc), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, Caprylic glyceride, oleoyl-polyoxyl-6-glycerides, lauroyl polyoxyl-6-gylcerides, polyglyceryl-3-dioleate, diethylene glycol monoethyl ether, propylene glycol monolaurate type I etc, cyclodextrins, polyhydric alcohol, especially 1,2-propanediol, butanediol, glycerine, polyethylene glycol (m.w. 100 and higher), Dimethyl Sulfoxide, Dimethyl Isosorbide, tetrahydrofurfuryl alcohol, diethyl tolumide, monoisopropylidene glycerine and others Solubilizers, surfactants, emulsifying agents, dispersing agents and similar compounds or chemicals known to those skilled in the art can be used either alone or in combination thereof Example 21

Oral bioavailability of THC is only 10-20%. For our calculation purpose, we took an average bioavailability of 15% 17. Accordingly, the actual dose delivering to patient upon oral delivery is described in Table 17:

TABLE 17

Theoretical dose required from Transdermal Dosage form.

| Oral Dose | Transdermal Dose range (mg/day) |
|---|---|
| 5 mg/day | 0.75 |
| 10 mg/day | 1.5 |
| 20 mg/day | 3 |

Flux Required=Dose/Surface area=3.0 mg/day/surface area=3000 ug/24 hr/50 sqcm=2.5 ug/sqcm/hr Accordingly, 50 sqcm patch with 2.5 µg/sqcm/hr flux will deliver 3 mg of drug in one day through transdermal route which is equivalent to 20 mg/day oral dose. According to table, The maximum dose of approved dronabinol is 20 mg/day which is feasible to deliver through this formulation.

What is claimed is:

1. A method for the treatment and/or control of nausea and/or vomiting associated with cancer chemotherapy and/or anorexia associated with weight loss in patients with AIDS, comprising:
    selecting a patient in need of the treatment and/or control of nausea and/or vomiting associated with cancer chemotherapy and/or anorexia associated with weight loss in patients with AIDS;
    topically applying or instructing to topically apply a pharmaceutical composition in the form of a transdermal matrix patch comprising: dronabinol, wherein the concentration of the dronabinol is from about 1% to about 15% w/w;
    wherein the pharmaceutical composition further comprises:
        about 10% to about 17% w/w of a solvent comprising propylene glycol;
        about 4% to about 10% w/w of a penetration enhancer comprising oleic acid;
        about 50% to about 80% w/w of a silicone pressure sensitive adhesive;
        at least one suspending agent comprising silicon dioxide;
        an antioxidant comprising BHT,
    wherein the transdermal matrix patch provides an average flux of the dronabinol of about 0.43 to about 0.93 µg/cm$^2$/hr over at least 6 days,
    wherein said applying achieves topical delivery of dronabinol for the treatment and/or control of nausea and/or vomiting associated with cancer chemotherapy and/or anorexia associated with weight loss in patients with AIDS.

2. The method of claim 1, wherein the pharmaceutical composition is topically applied once in a day, once in two days, once in three days, once in four days, once in five days, once in six days, once in a week, or once in ten days.

3. The method of claim 1, wherein the pharmaceutical composition is topically applied two to six times in a day, once in a day, once in two days, once in three days, once in four days, once in five days, once in six days, once in a week.

4. The method of claim 1, wherein the pharmaceutical composition is a transdermal delivery system.

\* \* \* \* \*